United States Patent
Okamura et al.

(10) Patent No.: US 10,702,677 B2
(45) Date of Patent: Jul. 7, 2020

(54) INTRODUCER SHEATH AND INTRODUCER

(71) Applicant: TERUMO KABUSHIKI KAISHA, Shibuya-ku, Tokyo (JP)

(72) Inventors: Ryo Okamura, Shizuoka (JP); Tatsuya Ouchi, Shizuoka (JP); Keisuke Yoshida, Shizuoka (JP); Daisuke Nakashima, Shizuoka (JP); Katsuaki Soma, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 248 days.

(21) Appl. No.: 15/638,078

(22) Filed: Jun. 29, 2017

(65) Prior Publication Data

US 2018/0001061 A1 Jan. 4, 2018

(30) Foreign Application Priority Data

Jun. 30, 2016 (JP) ................. 2016-131057

(51) Int. Cl.
*A61M 25/00* (2006.01)
*A61M 25/06* (2006.01)
(Continued)

(52) U.S. Cl.
CPC ....... *A61M 25/0662* (2013.01); *A61L 29/041* (2013.01); *A61M 25/0054* (2013.01); *A61M 25/0097* (2013.01); *A61M 29/02* (2013.01); *A61M 39/22* (2013.01); *A61M 25/0045* (2013.01); *A61M 2025/0046* (2013.01); *A61M 2025/0098* (2013.01); *A61M 2039/229* (2013.01)

(58) Field of Classification Search
CPC ...... A61M 2025/0098; A61M 25/0054; A61M 25/0662
See application file for complete search history.

(56) References Cited

U.S. PATENT DOCUMENTS 6,068,622 A * 5/2000 Sater ................. A61M 25/0009
604/524
2003/0050681 A1* 3/2003 Pianca ................... A61N 1/056
607/125
(Continued)

FOREIGN PATENT DOCUMENTS

JP H04-065553 U 6/1992
JP H09-225036 A 9/1997
(Continued)

OTHER PUBLICATIONS

Office Action (Notice of Reasons for Refusal) dated Jan. 7, 2020, by the Japanese Patent Office in corresponding Japanese Patent Application No. 2016-131057 and an English Translation of the Office Action. (8 pages).

*Primary Examiner* — William R Carpenter
(74) *Attorney, Agent, or Firm* — Buchanan Ingersoll & Rooney PC (57) ABSTRACT

An introducer sheath is disclosed, which includes a tube body that is percutaneously inserted into a body lumen; and a hub that is connected to a proximal portion of the tube body. The tube body contains a polyvinylidene fluoride resin, a ratio of a thickness to an inner diameter of the tube body is $1/16$ or lower, and a ratio of a kink radius to an outer diameter of the tube body is 9.5 or lower.

17 Claims, 6 Drawing Sheets

(51) Int. Cl.
*A61L 29/04* (2006.01)
*A61M 29/02* (2006.01)
*A61M 39/22* (2006.01)

(56) References Cited

U.S. PATENT DOCUMENTS

| | | | | |
|---|---|---|---|---|
| 2007/0005001 | A1* | 1/2007 | Rowe | A61M 25/0014 |
| | | | | 604/19 |
| 2013/0172851 | A1* | 7/2013 | Shimada | A61M 25/0053 |
| | | | | 604/508 |
| 2014/0025003 | A1* | 1/2014 | Kimmel | A61M 25/0043 |
| | | | | 604/96.01 |
| 2014/0114290 | A1* | 4/2014 | Okamura | A61M 25/0662 |
| | | | | 604/528 |
| 2016/0058976 | A1 | 3/2016 | Okamura et al. | |
| 2016/0361517 | A1* | 12/2016 | Yazaki | A61M 25/0097 |

FOREIGN PATENT DOCUMENTS

| | | |
|---|---|---|
| JP | 2007-144062 A | 6/2007 |
| WO | 2013/002286 A1 | 1/2013 |
| WO | WO 2014/119527 A1 | 8/2014 |
| WO | 2015/133281 A1 | 9/2015 |

* cited by examiner

INTRODUCER SHEATH AND INTRODUCER

CROSS-REFERENCES TO RELATED APPLICATIONS

This application claims priority to Japanese Application No. 2016-131057 filed on Jun. 30, 2016, the entire content of which is incorporated herein by reference.

TECHNICAL FIELD

The present disclosure relates to an introducer sheath used in an introducer as a medical instrument and an introducer including the introducer sheath and a dilator.

BACKGROUND DISCUSSION

In the related art, a medical instrument called an introducer has been used for introducing a catheter into a body lumen. The introducer is configured to include an introducer sheath provided with a hollow tube body generally called a sheath tube and a hub provided in the tube body, and a dilator used by being assembled with the introducer sheath.

The tube body of the introducer sheath is percutaneously introduced into the body lumen (for example, a blood vessel) from a distal side. A hollow portion (lumen) formed inside the tube body is used as an access passage that communicates with the inside and the outside of the living body. Regarding a use of the introducer sheath, it is preferable that the tube body has a large inner diameter and small outer diameter, that is, has a thickness to the smallest extent. The tube body is formed to have a large inner diameter, thereby making it possible to secure a large cross-sectional area of the hollow portion. Therefore, an instrument such as a catheter can be smoothly introduced through the hollow portion, and an instrument such as a catheter can cope with having a large outer diameter. On the other hand, the tube body is formed to have a small outer diameter, thereby having insertion resistance into the body lumen. Therefore, insertion properties into the body lumen improve, and further a minimally invasive procedure can be realized because a small puncture is formed in a puncture site.

However, when the thickness of the tube body is formed to be thin to some extent, the tube body has a decrease in rigidity against bending of the tube body. Therefore, the tube body is likely to kink. In a procedure in which the introducer is used, the distal side of the tube body of the introducer sheath indwells in a puncture site, and then an instrument such as a catheter is introduced into the body lumen via the hub. Therefore, when the medical instrument is introduced into the hollow portion of the tube body, the tube body needs to have kink resistance such that the tube body does not kink on the proximal side. For example, International Publication No. WO2014/119527 proposes an introducer sheath having a configuration in which, even though a tube body kinks, a kinked portion of the tube body can be restored to the extent that an inner diameter is the same as an original diameter when pressure applied to the tube body from outside is canceled.

SUMMARY

As described above, from a viewpoint of performance improvement, it is preferable that the tube body of the introducer sheath has a large inner diameter and a thickness to the thinnest extent; however, a problem can arise in that the kink resistance decreases depending on a decrease in the thickness.

For example, when the tube body is formed by using a hard material such that the tube body has high kink resistance, the tube body lacks flexibility, and the lack of flexibility results in a decrease in followability to a body lumen and an increase in suffering of a patient. On the other hand, when the tube body is formed by using a soft material, the kink resistance decreases. Therefore, it can be difficult for the tube body to have a large inner diameter and to have a small thickness.

Hence, in consideration of physical properties of a material of which the tube body is made, the tube body of the introducer sheath needs to have appropriately set inner diameter and thickness so as to have desired kink resistance.

An introducer sheath is disclosed, which includes a tube body that is formed to have a larger inner diameter and a smaller thickness than those of a tube body in the related art and that achieves improvement of kink resistance.

According to the present disclosure, there is provided an introducer sheath including: a tube body that is percutaneously inserted into a body lumen; and a hub that is connected to a proximal portion of the tube body. The tube body contains a polyvinylidene fluoride resin, and thickness/inner diameter of the tube body is $1/16$ or lower, and kink radius/outer diameter of the tube body is 9.5 or lower.

The tube body according to the present disclosure is formed to have a ratio of thickness/inner diameter that is lower than that of a tube body in the related art, that is, to have a predetermined thickness or smaller. Further, the tube body has a small ratio of kink radius/outer diameter, that is, has improvement in the kink resistance. Therefore, according to the present disclosure, it is possible to provide the introducer sheath including a tube body that is formed to have a larger inner diameter and a smaller thickness than those of the tube body in the related art and that achieves improvement of kink resistance.

DETAILED DESCRIPTION OF THE PREFERRED EMBODIMENT

Hereinafter, an introducer sheath 100 according to the embodiment is described with reference to figures.

FIGS. 1 to 3B are views for illustrating portions of the introducer sheath 100, and FIGS. 4 to 6B are views to be provided for the description of an example.

Figure 2:
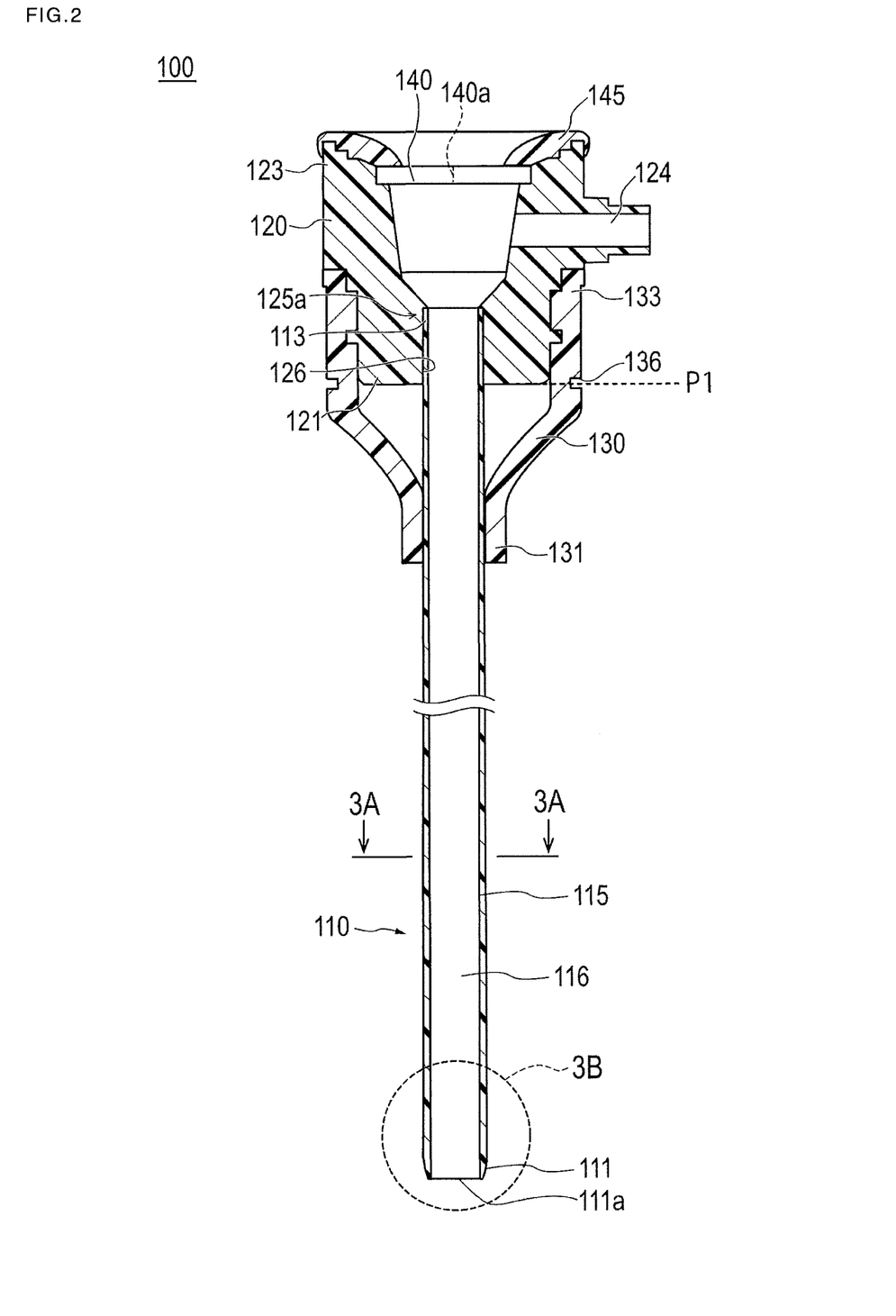
FIG. 2 is a cross-sectional view in an axial direction of an introducer sheath according to the embodiment.

With reference to FIG. 2, in the present specification, a side (upper side in FIG. 2) in the introducer sheath 100, on which a hub 120 is disposed, is referred to as a "proximal side". A side (lower side in FIG. 2), which is positioned on a side opposite to the proximal side in the introducer sheath 100 and on which introduction into a living body is performed, is referred to as a "distal side". In addition, a direction (vertical direction in FIG. 2), in which the introducer sheath 100 extends, is referred to as an "axial direction". In addition, in the description of the specification, a "distal portion" means a certain range containing a distal end (most distal end) and the periphery thereof, a "proximal portion" means a certain range containing a proximal end (most proximal end) and the periphery thereof.

Figure 1:
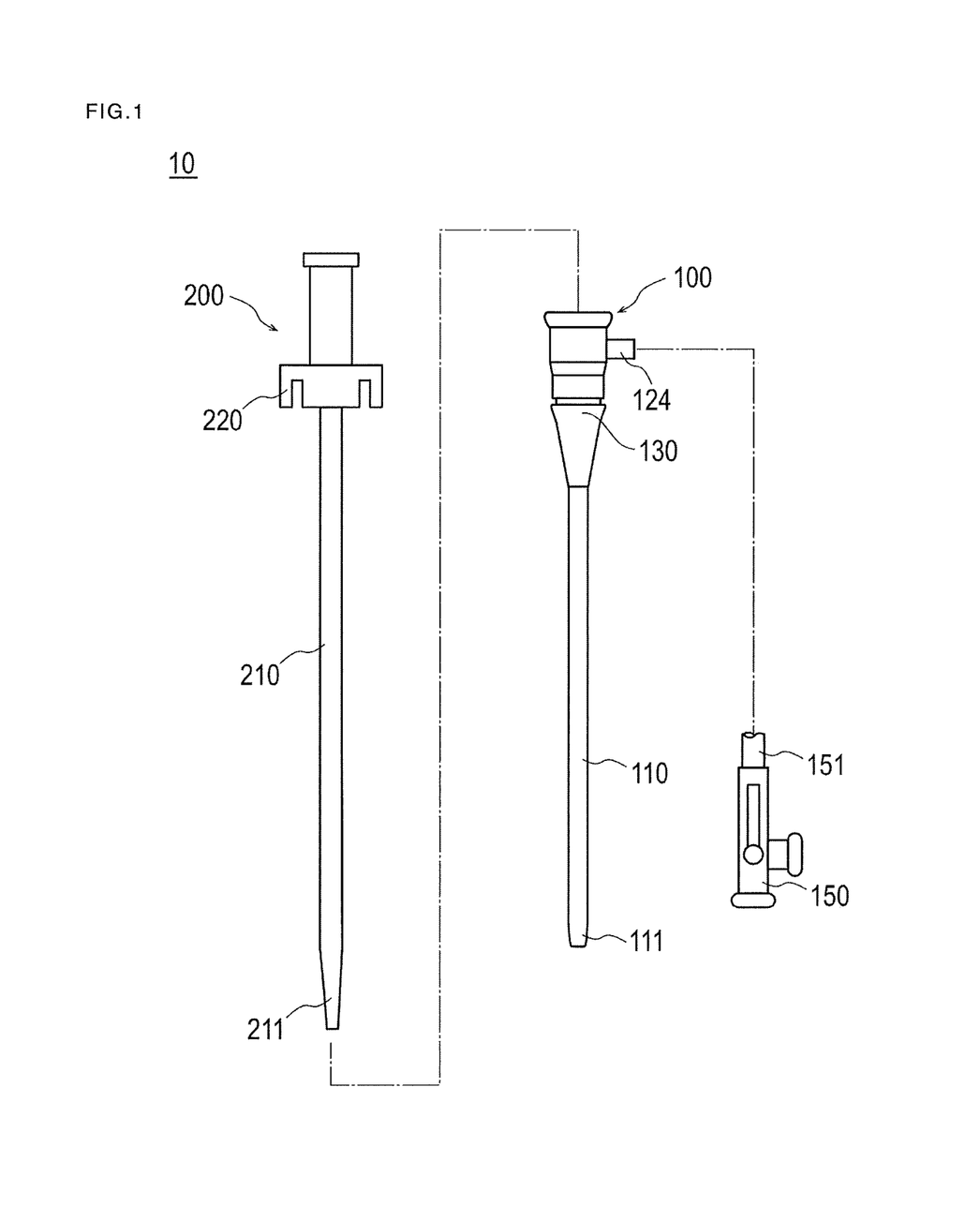
FIG. 1 is a view showing an introducer according to an embodiment.

As shown in FIG. 1, an introducer 10 according to the embodiment includes the introducer sheath 100 and a dilator 200.

The introducer sheath 100 indwells in a body lumen of a blood vessel and is used for inserting and introducing an instrument such as a catheter or a guide wire into the body lumen through the inside of the introducer sheath.

As shown in FIG. 2, the introducer sheath 100 can include a tube body (sheath tube) 110 provided with a hollow portion (lumen) 116 that extends in an axial direction, a hub (sheath hub) 120 that is connected to the proximal side of the tube body 110, and a strain relief portion 130 that is supported on the distal side of the hub 120 and surrounds a proximal portion 113 (also referred to as a tube proximal portion) of the tube body 110.

The tube body 110 is formed by a substantially cylindrical tube shaped member. As shown in FIG. 2, the tube body 110 is provided with a tapered tube distal portion 111, a tube main body portion 115 that is positioned on the proximal side of the tube distal portion 111, and a tube proximal portion 113 that is positioned on the proximal side of the tube main body portion 115 and is interlocked with the hub 120. The tube distal portion 111 is provided with a distal opening portion 111a formed on the distal end thereof.

Figure 3A:
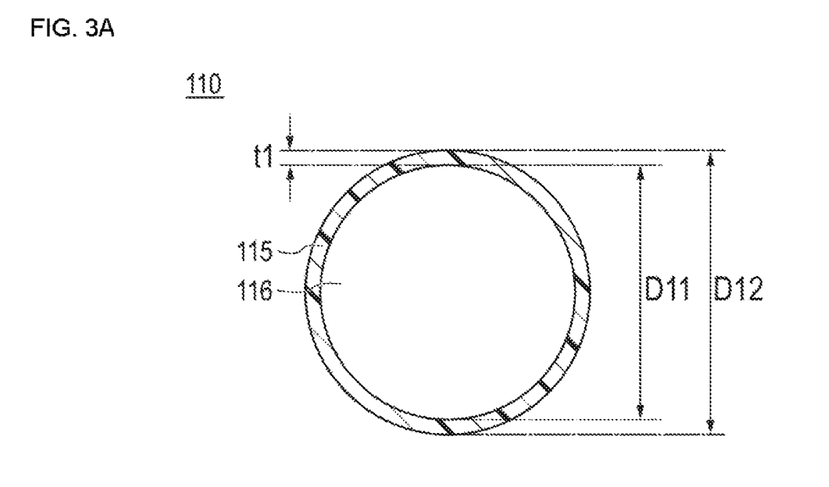
FIG. 3A is a cross-sectional view taken along line 3A-3A in FIG. 2.
Figure 3B:
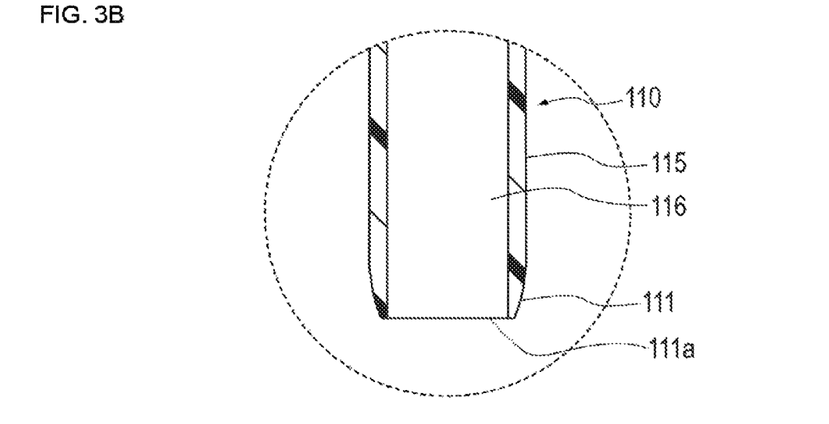
FIG. 3B is an enlarged view of dashed line portion 3B in FIG. 2.

FIG. 3A shows a cross-sectional view (an axially orthogonal cross-sectional view) of the tube main body portion 115, which is taken along line 3A-3A in an arrow direction in FIG. 2. In addition, FIG. 3B shows an enlarged section of a portion of dashed line portion 3B in FIG. 2.

The tube main body portion 115 of the tube body 110 is formed to have substantially constant sizes in the axial direction with dimensions (an inner diameter D11, an outer diameter D12, and a thickness t1) shown in FIG. 3A. In accordance with an exemplary embodiment, as shown in FIG. 3B, the tube distal portion 111 of the tube body 110 has a tapered shape with a constant inner diameter and an outer diameter that tapers toward the distal side. As will be described below, the tube proximal portion 113 of the tube body 110 is fixed to the hub 120.

Note that dimensional examples of the tube main body portion 115, which will be described below mean dimensional examples obtained before the tube body 110 is fixed to the hub 120.

As shown in FIG. 2, the hub 120 is provided with a lumen 126 to which the tube proximal portion 113 is fixed, and a side port 124 that communicates with the lumen 126.

One end of a flexible tube 151 (refer to FIG. 1) is connected to the side port 124 in an airtight manner. For example, a three-way stopcock 150 is mounted on the other end of the tube 151. In accordance with an exemplary embodiment, a liquid such as a physiological salt solution can be injected from a port of the three-way stopcock 150 via the tube 151 into the hollow portion 116 of the tube body 110. It is possible to configure the tube 151 to have a known tube made of polyvinyl chloride.

There is no particular limitation on a constituent material of the hub 120, and, a hard material such as a hard resin is preferably used. Specific examples of the hard resin include a polyolefin such as polyethylene or polypropylene, polyamide, polycarbonate, or polystyrene.

The proximal portion 123 of the hub 120 is provided with a valve body 140 that is attached to prevent a liquid such as blood flowing into the tube body 110 from leaking. The valve body 140 is configured of an elastic member provided with a slit 140a into which a dilator main body 210 can be inserted. The valve body 140 is formed to have a substantially elliptical membrane shape (disc shape) and is fixed to the hub 120 in a liquid-tight manner with a predetermined cap 145 to be fitted in.

There is no particular limitation on a constituent material of the valve body 140, and examples of the material include silicone rubber, latex rubber, butyl rubber, or isoprene rubber, as an elastic member.

The tube proximal portion 113 is fixed to an interlock portion 125a of the hub 120. The interlock portion 125a between the tube proximal portion 113 and the hub 120 can be fixed, for example, with an adhesive.

As shown in FIG. 2, the strain relief portion 130 is externally fitted to the tube body 110 and the hub 120. A distal portion 131 of the strain relief portion 130 is disposed to surround a certain range of the tube body 110 on the proximal side. In addition, a proximal portion 133 of the strain relief portion 130 is disposed to surround a certain range of the hub 120 on the distal side and covers the interlock portion 125a in which the tube body 110 is interlocked with the hub 120.

The strain relief portion 130 is provided with a concave portion 136 at a position that overlaps a distal end P1 of the hub 120 in the axial direction. Note that the distal end P1 of the hub 120 can be used as a reference for determining a pressing position of the tube body 110 (refer to FIG. 5) when a measurement test of a kink generation angle, which will be described below, is conducted.

There is no particular limitation on a constituent material of the strain relief portion 130, and examples thereof include natural rubber or silicone resin.

As shown in FIG. 1, the dilator 200 is provided with the dilator main body 210 that is configured to have a tube shaped body so as to be insertable into the tube body 110, and a dilator hub 220 configured to be connected to the hub 120.

The dilator 200 is used to prevent the tube body 110 from being folded or to widen a puncture in skin when the tube body 110 of the introducer sheath 100 is inserted into the body lumen.

When the dilator main body 210 is inserted into the tube body 110, a distal portion 211 of the dilator main body protrudes from the distal opening portion 111a of the tube body 110. The distal portion 211 of the dilator main body 210 is formed to have a tapered shape that tapers toward the distal side.

There is no particular limitation on a constituent material of the dilator main body 210, and the same material as that used in a member in the related art as the dilator main body 210 can be used. Specific examples include a polyolefin such as polypropylene (PP) or polyethylene (PE), nylon, polyester such as polyethylene terephthalate (PET), or a fluoropolymer such as polyvinylidene fluoride (PVDF) or tetrafluoroethylene-hexafluoropropylene copolymer (FEP). Of the example, the fluoropolymer is preferable, and a material having hardness equal to or higher than that of the polyvinylidene fluoride (PVDF) is preferable.

There is no particular limitation on a constituent material of the dilator hub 220, and a hard material such as a hard resin is preferably used. Specific examples of the hard resin include a polyolefin such as polyethylene or polypropylene, polyamide, polycarbonate, or polystyrene.

Next, the tube body 110 will be described in detail.

In accordance with an exemplary embodiment, the tube body 110 contains a polyvinylidene fluoride resin. Here, the "polyvinylidene fluoride resin" means a polymer having a building block (hereinafter, referred to as a "building block A") derived from vinylidene fluoride ($CH_2=CF_2$) or vinylidene trifluoride ($CHF=CF_2$).

There is no particular limitation on the polyvinylidene fluoride resin as long as the polyvinylidene fluoride resin has the building block A and has the hardness higher than that of an ethylene tetrafluoroethylene (ETFE) resin (copolymer of tetrafluoroethylene ($C_2F_4$)) and ethylene ($C_2H_4$) used in the sheath in the related art. Specifically, it is preferable that the polyvinylidene fluoride resin is a copolymer of a polymer; building block A which consists of a building block (building block A) derived from vinylidene fluoride ($CH_2=CF_2$) or vinylidene trifluoride ($CHF=CF_2$); and a building block (building block B) derived from a formula $CF_2=CX_2$ (X represents a halogen atom or an alkyl halide group, independently from each other). It is possible to more effectively increase the hardness of the tube body 110 by containing ethylene units having more halogen atoms. Here, examples of a compound represented by the formula: $CF_2=CX_2$ include tetrafluoroethylene (TFE), chlorotrifluoroethylene (CTFE), or hexafluoropropylene (HFP). Each of materials of the building block A and the building block B may be one single type or two or more types. In addition, with the copolymer that consists of the building block A and the building block B described above, there is no particular limitation on composition of the copolymer; however, the building block B is contained at a ratio of preferably 15 mol % to 85 mol %, more preferably 30 mol % to 80 mol % with respect to a total building block (a total sum of the building block A and the building block B is 100 mol %).

For example, a material containing the ethylene tetrafluoroethylene resin has been known as a material of which the tube body is made. Since the tube body made of the material is relatively flexible, it can be difficult to insert the tube body into the body lumen because the tube body is bent due to the flexibility when the tube body is inserted into the body lumen by using the dilator. In accordance with an exemplary embodiment, the tube body 110 that contains the polyvinylidene fluoride resin has a certain degree of hardness. Therefore, when the tube body 110 containing the polyvinylidene fluoride resin and the dilator 200 are combined so as to configure the introducer 10, the introducer has strong elasticity. Hence, it is possible to reduce bending of the tube body 110 and it is possible to easily and smoothly perform the insertion into the body lumen.

In accordance with an exemplary embodiment, it is possible to form a coating layer having lubricity on an outer surface and/or an inner surface of the tube body 110. It is possible to use a known coating material in the related art with hydrophilicity or hydrophobicity as a material of which the coating layer is made. Dimensional examples, which will be described below, mean dimensions of the tube body 110 that does not include a dimension (thickness) of the coating layer in a case where the coating layer is formed on the tube body 110.

With reference to FIG. 3A, in the tube body 110, thickness t1/inner diameter D11 (a ratio of the thickness t1 to the inner diameter D11) of the tube main body portion 115 is equal to or smaller than 1/16 (0.0625). Preferably, thickness t1/inner diameter D11 of the tube main body portion 115 is 1/25 (0.0400) to 1/20 (0.0500).

There is no particular limitation on the dimensions of the tube main body portion 115 as long as thickness t1/inner diameter D11 of the tube main body portion 115 is 1/16 (0.0625), and, for example, the tube main body can be formed with the following dimensions.

In accordance with an exemplary embodiment, the tube main body portion 115 can be formed to have the inner diameter D11 of 1.9 mm to 2.5 mm. In this case, preferably, the thickness t1 is 0.050 mm to 0.140 mm, and an outer diameter D12 is 2.0 mm to 2.78 mm. In addition, it is possible to form the tube main body portion 115 to have the inner diameter D11 of 1.1 mm to 2.0 mm. In this case, preferably, the thickness t1 is 0.050 mm to 0.120 mm, and an outer diameter D12 is 1.2 mm to 2.14 mm.

In the embodiment, kink radius Rk/outer diameter D12 (a ratio of the kink radius Rk to the outer diameter D12) of the tube main body portion 115 is 9.5 or lower. Preferably, kink radius Rk/outer diameter D12 of the tube main body portion 115 is 9.1 or lower. In a case where the inner diameter D11 is assumed to be constant, kink resistance of the tube main body portion 115 depends on a size of the thickness t1, that is, the outer diameter D12. Therefore, the larger the outer diameter D12, the more the kink resistance improves. Since kink radius Rk/outer diameter D12 of the tube main body portion 115 of the embodiment is relatively small to be 9.5 or lower, the kink resistance improves in a case where the thickness t1 and the outer diameter D12 are used as references. Note that a method of measuring the kink radius Rk will be described below.

Figure 5:
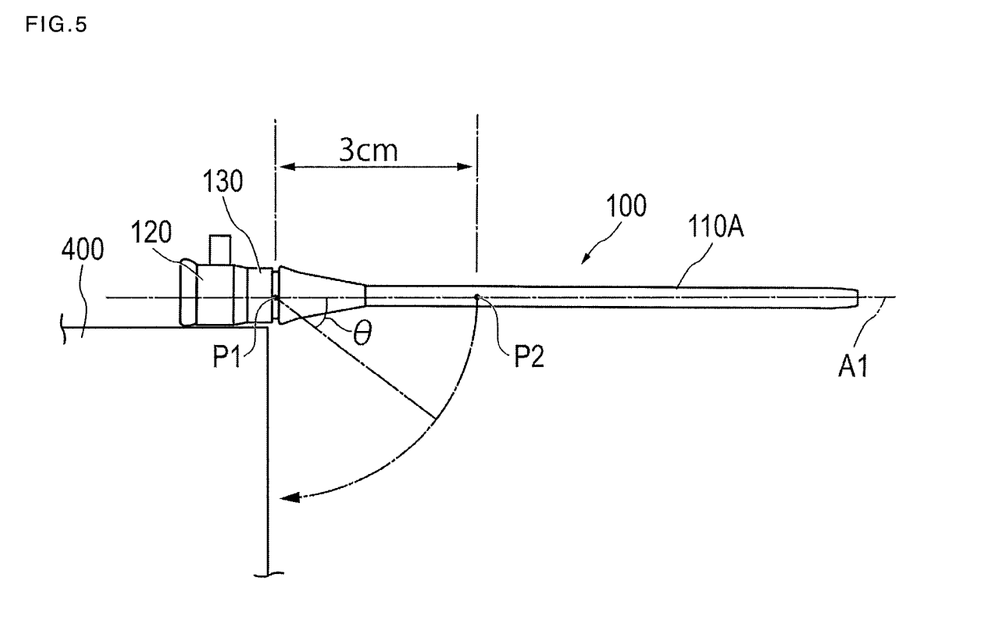
FIG. 5 is a schematic diagram showing a method of measuring a kink generation angle.

In addition, in the embodiment, the tube body 110 has a kink generation angle θ of 38° or larger when the tube body is pressed at a position that is 3 cm away from the distal end P1 of the hub 120 (refer to FIG. 5). Therefore, since the kink resistance of the tube body 110 increases in a state in which the introducer sheath 100 is held or fixed on the proximal side of the introducer sheath 100, it is possible to appropriately prevent generation of the kink on the proximal side of the tube body 110 while the tube body 110 is inserted into the body lumen and various operations are performed. Note that a method of measuring the kink generation angle θ will be described below.

In addition, in the embodiment, a material, of which the dilator main body 210 is made, has flexural modulus (ISO178 JIS K7171) higher than a material, of which the tube body 110 is made. Therefore, when the tube body 110 is inserted into the body lumen in a state in which the dilator main body 210 is inserted into the hollow portion 116 of the tube body 110 so as to form the introducer 10, strong elasticity is applied to the tube body 110 due to the dilator main body 210, and thus, the tube body 110 can be prevented from being folded or being kinked. Note that, in a case where tube shaped members having the same inner diameter and the same outer diameter are compared to each other, a magnitude relationship of the flexural moduli described above also means that the tube shaped member made of the material, of which the dilator main body 210 is made, has the flexural modulus higher than the tube shaped member made of the material of which the tube body 110 is made.

In addition, in the embodiment, the tube body 110 is configured to be provided with the tube distal portion 111 that is harder than the tube main body portion 115. Since the tube distal portion 111 is formed to have a tapered shape in which the outer diameter thereof decreases toward the distal side, it can be relatively easy for the tube distal portion 111 to be folded when the tube body 110 is inserted into the body lumen. In addition, the tube distal portion 111 is formed to have the tapered shape, and thereby the kink resistance decreases more than that of the tube main body portion 115. Therefore, in the embodiment, the tube distal portion 111 is formed to be harder than the tube main body portion 115, the tube distal portion 111 is prevented from being folded when the tube body 110 is inserted into the body lumen. In such a configuration described above, the tube distal portion 111 also has improvement in the kink resistance.

Next, the present disclosure will be more specifically described with Examples; however, the present disclosure is not limited thereto.

Test for Measuring Kink Radius

Measurement of the kink radius Rk of tube bodies of the following Examples 1 to 3 and a tube body of the following comparative example (hereinafter, the tube bodies of Examples and the comparative example are collectively referred to as a "tube body 110A") was conducted.

(1) A tube body of Example 1: made of the polyvinylidene fluoride (PVDF) resin, the thickness t1=0.10 mm, the inner diameter D11=1.753, and the outer diameter D12=1.773 mm.

(2) A tube body of Example 2: made of the polyvinylidene fluoride (PVDF) resin, a thickness t1=0.10 mm, an inner diameter D11=2.213, and an outer diameter D12=2.413 mm.

(3) A tube body of Example 3: made of the polyvinylidene fluoride (PVDF) resin, the thickness t1=0.12 mm, the inner diameter D11=2.245 mm, and the outer diameter D12=2.485 mm.

(4) A tube body of the comparative example: made of the ethylene tetrafluoroethylene (ETFE) resin, the thickness t1=0.12 mm, the inner diameter D11=2.38, and the outer diameter D12=2.62 mm.

Figure 4:
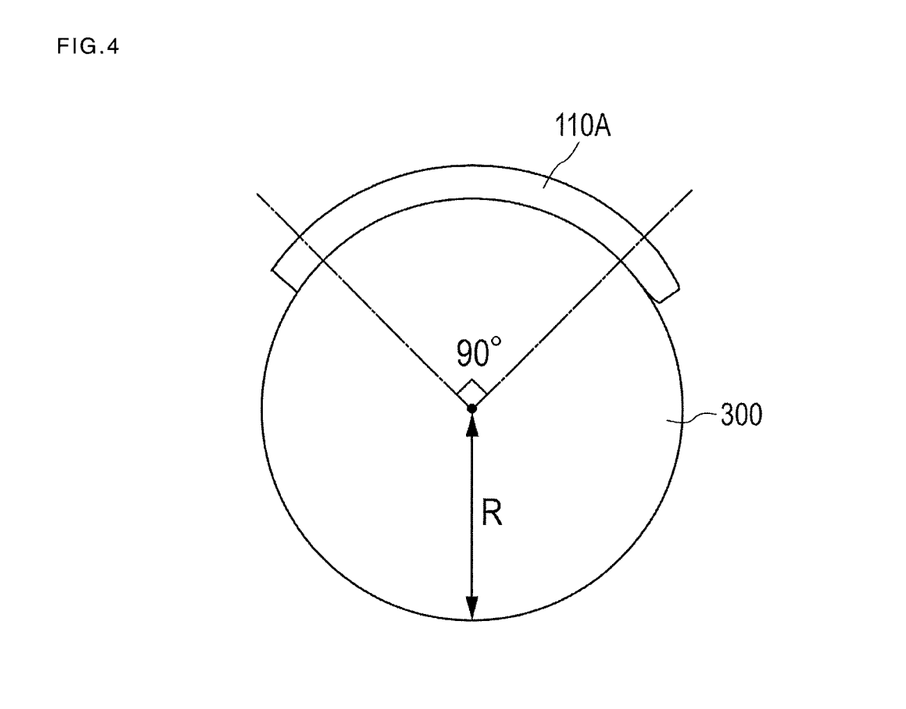
FIG. 4 is a schematic diagram showing a method of measuring a kink radius.

In the measurement test of the kink radius Rk, a test instrument 300 formed by a circular member illustrated in FIG. 4 was used. With the test instrument 300 having a radius R of 150 mm to 5 mm, presence or absence of a kink of the tube body 110A was searched for when the tube body 110A was folded by 90° with respect to the center of the test instrument 300 along the tube body 110A on the test instrument 300. The test was performed seven times for each of Examples 1 to 3 and the comparative example. Table 1 shows test results.

TABLE 1

| | Kink radius Rk (mm) | | | |
| --- | --- | --- | --- | --- |
| | Example 1 | Example 2 | Example 3 | Comparative example |
| Test 1 | 13 | 20 | 20 | 25 |
| Test 2 | 10 | 20 | 20 | 25 |
| Test 3 | 15 | 20 | 20 | 30 |
| Test 4 | 9 | 20 | 20 | 25 |
| Test 5 | 13 | 20 | 20 | 25 |
| Test 6 | 12 | 20 | 20 | 25 |
| Test 7 | 11 | 20 | 15 | 25 |
| Maximum value | 15 | 20 | 20 | 30 |
| Minimum value | 9 | 20 | 15 | 25 |
| Outer diameter (mm) of tube body | 1.773 | 2.413 | 2.485 | 2.62 |
| Maximum kink radius Rk/outer diameter of tube body | 8.46 | 8.29 | 8.05 | 11.45 |
| Minimum kink radius Rk/outer diameter of tube body | 5.08 | 8.29 | 6.04 | 9.54 |

Figure 6A:
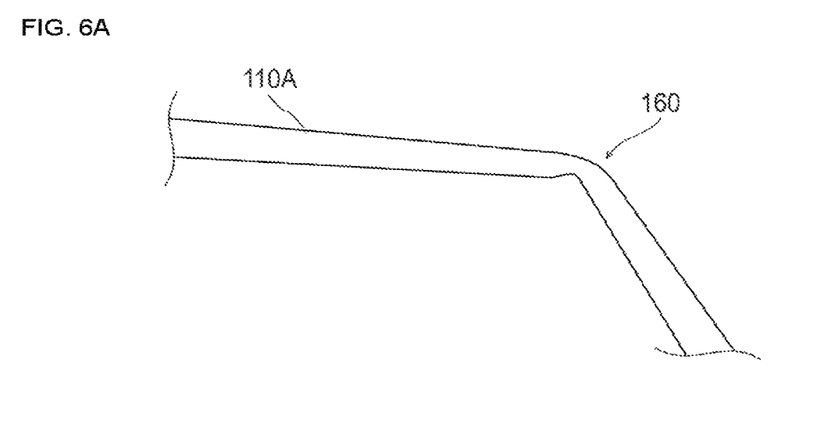
FIG. 6A is a side view of a tube body for illustrating a kinked portion formed in the tube body.
Figure 6B:
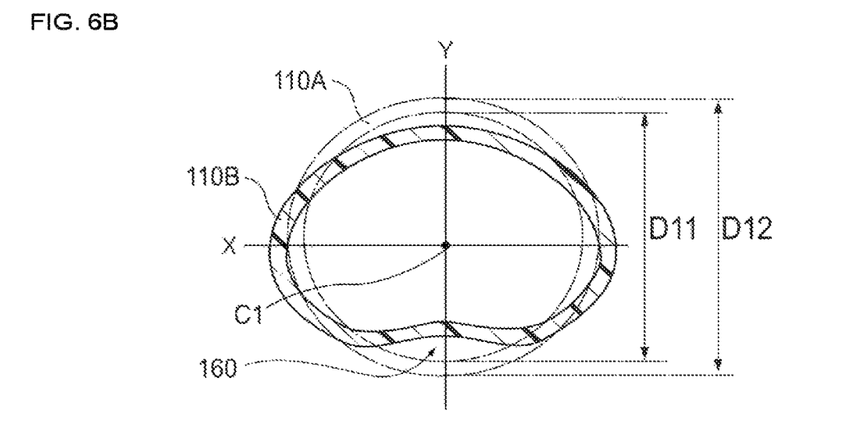
FIG. 6B is a cross-sectional view of the tube body for illustrating the kinked portion formed in the tube body.

The kink radii Rk shown in Table 1 are curvature radii measured when kinks are generated in Examples 1 to 3 and the comparative example. In other words, the kink radius Rk is a radius R of the test instrument 300 used when the kink is generated in the tube body 110A. Note that the determination of the presence or absence of the kink generation is performed whether or not a kinked portion 160 is formed in the tube body 110A as shown in FIGS. 6A and 6B. As illustrated in FIG. 6B, a tube body 110B obtained after the kink generation has a shape that is flat in an X-axial direction or a Y-axial direction through the center C1 of the tube body 110A on an axially orthogonal cross section, compared to the tube body 110A obtained before the kink generation. As a result of the measurement test, in a case where deformation of the tube body 110A into a flat shape was verified, the kink generation in the tube body 110A was determined. However, the cross-sectional shape shown in FIG. 6B is provided as an example when the kink is generated, and thus the kink generation in the tube body 110A was determined with a shape other than the shape shown in FIG. 6B, in a case where a flat shape (crushed shape) is formed, compared to the shape obtained before the kink generation.

As can be verified in Table 1, when Example 3 in which the thickness is formed to be 0.12 mm is compared to the comparative example in which the thickness is formed to be 0.12 mm, it is possible to know that Example 3 has the minimum value and the maximum value of the kink radius Rk which are both smaller than those of the comparative example, that is, the kink resistance is higher. As a result, it is possible to know that the kink resistance of the tube body 110A more improves in a case where the polyvinylidene fluoride resin is used as the material of which the tube body 110A is formed than in a case of using the ethylene tetrafluoroethylene resin as the material thereof.

In addition, the maximum values of the kink radii Rk of Examples 1 to 3 were smaller than the maximum value of the kink radius Rk of the comparative example, and the minimum values of the kink radii Rk of Examples 1 to 3 were smaller than the minimum value of the kink radius Rk of the comparative example. As a result, in a case where the polyvinylidene fluoride resin is used as the material of which the tube body 110A is formed, it is possible to know that the kink resistance of the tube body 110A tends to be more improved.

In addition, when Example 2 is compared to Example 3, it is possible to verify that both have the same degree of the kink resistance, regardless of the smaller thickness in Example 2. In this manner, the polyvinylidene fluoride resin is used as the material of which the tube body 110A is formed, and thereby it is possible to know that an influence of the kink resistance on the thinness of the thickness decreases. Hence, the polyvinylidene fluoride resin is used to form the tube body 110A, and thereby it is possible to know that it is possible to secure desired kink resistance in a case where the tube body 110A is formed to have the small thickness.

As can be verified in Table 1, it is possible to verify that a ratio of the minimum values of the kink radii Rk to the outer diameters of Examples 1 to 3 is 9.5 or lower. Hence, in the case where the polyvinylidene fluoride resin is used as the material of which the tube body 110A is formed, it is possible to obtain appropriate kink resistance with the minimum value of the kink radius Rk of about 9 to 20 mm in the tube body 110A of Examples 1 to 3 as long as the ratio of the minimum value of the kink radius Rk to the outer diameter is 9.5 or lower.

In a procedure in which the introducer sheath 100 indwells in a radial artery such that an instrument such as a catheter is introduced into the brachial artery or the aorta, the introducer sheath has a puncture angle of 30° in general, and the tube body 110 is bent to a curvature radius of 80 mm during the procedure. In a case where the ratio of the minimum value of the kink radius Rk to the outer diameter is set to be 9.5 or lower such that the minimum value of the kink radius Rk is 9 to 20 mm, it is possible to prevent the tube body 110 from being kinked at least in the procedure.

Test for Measuring Kink Generation Angle

Measurement of the kink generation angle was performed in the introducer sheath 100 including the tube body 110A of the aforementioned Examples 1 to 3. The introducer sheath 100 used in the test has the same configuration as the configuration (refer to FIG. 2) described in the aforementioned embodiment. Specifically, the introducer sheath 100 for the test included the tube bodies 110A of Examples 1 to 3 that were each provided with the hub 120 and the strain relief portion 130.

As illustrated in FIG. 5, in the measurement test of the kink generation angle, in a state in which the hub 120 and a part of the strain relief portion 130 were fixed on a support table 400, the tube body was pressed by finger at a position P2 that was 3 cm away from the distal end P1 (refer to FIG. 2) of the hub 120, and the tube body 110A was bent downward until the tube body 110A was kinked. When the tube body 110A is kinked, a bending angle θ was measured with an axial core A1 of the tube body 110A as a reference, and the measurement result was used as the kink generation angle. Note that the absence or presence of the kink generation was verified with the same reference as that in the aforementioned measurement test of the kink radius Rk (refer to FIGS. 6A and 6B).

The tests were performed ten times for each of the introducer sheaths 100 including the tube bodies of Examples 1 to 3. Table 2 shows test results.

TABLE 2

| | Kink generation angle (°) | | |
| --- | --- | --- | --- |
| | Example 1 | Example 2 | Example 3 |
| Test 1 | 48 | 52 | 58 |
| Test 2 | 50 | 40 | 54 |
| Test 3 | 55 | 38 | 56 |
| Test 4 | 54 | 55 | 57 |
| Test 5 | 47 | 53 | 57 |
| Test 6 | 46 | 52 | 56 |
| Test 7 | 54 | 42 | 56 |
| Test 8 | 56 | 52 | 56 |
| Test 9 | 48 | 38 | 54 |
| Test 10 | 43 | 38 | 56 |
| Average value | 50.1 | 46 | 56 |
| Maximum value | 56 | 55 | 58 |
| Minimum value | 43 | 38 | 54 |

It is possible to verify that Example 2 has the minimum kink generation angle from the test result shown in Table 2, and the minimum angle is 38°. In addition, it is possible to verify that Example 3 has the maximum kink generation angle, and the maximum angle is 58°. In this manner, the polyvinylidene fluoride resin is used as the material of which the tube body 110A is formed, and thereby it is possible to improve the kink resistance of the tube body 110A such that even the minimum kink generation angle is 38°.

As described above, the tube body 110 according to the embodiment is formed to have a ratio of thickness/inner diameter that is lower than that of the tube body in the related art, that is, to have the predetermined thickness or smaller. Further, the tube body 110 has a small ratio of kink radius/outer diameter, that is, has improvement in the kink resistance. Therefore, according to the present disclosure, it is possible to provide the introducer sheath 100 including the tube body 110 that is formed to have the larger inner diameter and the smaller thickness than those of the tube body in the related art and that achieves improvement of kink resistance.

In addition, the tube body 110 is provided with the tapered tube distal portion 111 and the tube main body portion 115 positioned on the proximal side of the tube distal portion 111. In the tube body 110, thickness/inner diameter of the tube main body portion 115 is $\frac{1}{16}$ or lower, and kink radius/outer diameter of the tube main body portion 115 is 9.5 or lower. Therefore, it is possible to improve insertion properties into the body lumen from the tube distal portion 111, and it is possible to improve the kink resistance of the tube main body portion 115 with the small thickness of the tube main body portion 115 into which various types of medical tools are inserted.

In addition, since the tube distal portion 111 of the tube body 110 is configured to be harder than the tube main body portion 115, it is possible to prevent the tube distal portion 111 from being folded when the tube body 110 is inserted into the body lumen, and the kink resistance of the tube distal portion 111 improves.

In addition, the introducer sheath 100 includes the strain relief portion 130 that covers the interlock portion 125a between the tube body 110 and the hub 120. In the tube body 110, the proximal end of the tube body 110 is fixed to the lumen 126 of the hub 120, and the kink generation angle is 38° or larger when the tube body is pressed at a position that is 3 cm away from the distal end of the hub 120 in a state in which the strain relief portion 130 is provided. The strain relief portion 130 protects the interlock portion 125a between the tube body 110 and the hub 120 from outside, and adjusts a change in rigidity of the distal end P1 of the hub 120. Since the kink generation angle of the tube body 110 is 38° or larger, the kink resistance of the tube body 110 improves in a state in which the introducer sheath 100 is held or fixed on the proximal side of the introducer sheath 100.

In addition, the introducer 10 according to the embodiment includes the introducer sheath 100 provided with the tube body 110, and the dilator 200 provided with the dilator main body 210 that is insertable into the hollow portion 116 of the tube body 110. The material, of which the dilator main body 210 is made, has flexural modulus higher than the material, of which the tube body 110 is made. Therefore, when the tube body 110 is inserted into the body lumen in a state in which the dilator main body 210 is inserted into the hollow portion 116 of the tube body 110, strong elasticity is applied to the tube body 110 due to the dilator main body 210, and thus it is possible to prevent the tube body 110 from being folded or being kinked.

As described above, the introducer sheath according to the present disclosure is described in the embodiments; however, the present disclosure is not limited to the configurations described in the specification, and it is possible to perform appropriate modifications based on Claims.

For example, in the description of the embodiment, the tube body is provided with the tapered tube distal portion; however, the tube body may not have the tapered tube distal portion. In a case where the tube body does not have the tapered tube distal portion, the tube body is formed such that thickness/inner diameter of the tube body is 1/16 or lower all over the entire length in the axial direction, and kink radius/outer diameter of the tube main body portion is 9.5 or lower.

In addition, the specific structure of the introducer sheath or the specific structure of the dilator is not limited to the structure described as shown in figures, and it is possible to perform appropriate modifications as long as functions as the introducer are maintained.

In addition, as long as the introducer sheath according to the present disclosure includes the hub and the tube body that contains the polyvinylidene fluoride resin, thickness/inner diameter of the tube body is 1/16 or lower, and kink radius/outer diameter of the tube body is 9.5 or lower, there is no limitation on any configuration other than the configuration described above. Hence, it is possible to perform appropriate modifications on the dimensions or the physical properties, the materials, or the like of the members described above in the specification.

The detailed description above describes an introducer sheath used in an introducer as a medical instrument and an introducer including the introducer sheath and a dilator. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer sheath comprising:
   a tube body configured to be percutaneously inserted into a body lumen;
   a hub that is connected to a proximal portion of the tube body;
   a strain relief portion that is externally fitted to the tube body and hub, the strain relief portion covering an interlock portion in which the tube body is interlocked with the hub, the strain relief portion including a concave portion extending circumferentially around an outer surface of the strain relief portion at a position that overlaps a distal most end of the hub in an axial direction to permit the concave portion to be used as a reference for measuring a kink generation angle;
   the tube body comprises a polyvinylidene fluoride resin, and
   wherein a ratio of a thickness to an inner diameter of the tube body is 1/16 or lower, and a ratio of a kink radius to an outer diameter of the tube body is 9.5 or lower.

2. The introducer sheath according to claim 1,
   wherein the tube body is provided with a tapered tube distal portion and a tube main body portion positioned on the proximal side of the tube distal portion, and
   wherein a ratio of a thickness to an inner diameter of the tube main body portion is 1/16 or lower, and a ratio of a kink radius to an outer diameter of the tube main body portion is 9.5 or lower.

3. The introducer sheath according to claim 2,
   wherein the tapered tube distal portion of the tube body is harder than the tube main body portion.

4. The introducer sheath according to claim 3,
   wherein the tube body is configured to have a proximal end of the tube body that is fixed to a lumen of the hub, and the kink generation angle is 38° or larger when the tube body is pressed at a position that is 3 cm away from the distal end of the hub in a state in which the strain relief portion is provided.

5. The introducer sheath according to claim 2,
   wherein the tube body is configured to have a proximal end of the tube body that is fixed to a lumen of the hub, and the kink generation angle is 38° or larger when the tube body is pressed at a position that is 3 cm away from the distal end of the hub in a state in which the strain relief portion is provided.

6. The introducer sheath according to claim 1,
   wherein the tube body is configured to have a proximal end of the tube body that is fixed to a lumen of the hub, and a kink generation angle is 38° or larger when the tube body is pressed at a position that is 3 cm away from the distal end of the hub in a state in which the strain relief portion is provided.

7. The introducer sheath according to claim 1, wherein the strain relief portion is supported on a distal side of the hub and surrounds a proximal portion of the tube body.

8. An introducer comprising:
   an introducer sheath comprising a tube body configured to be percutaneously inserted into a body lumen, and a hub that is connected to a proximal portion of the tube body, wherein the tube body contains a polyvinylidene fluoride resin, and wherein a ratio of a thickness to an inner diameter of the tube body is 1/16 or lower, and a ratio of a kink radius to an outer diameter of the tube body is 9.5 or lower, and a strain relief portion that is externally fitted to the tube body and hub, the strain relief portion covering an interlock portion in which the tube body is interlocked with the hub, the strain relief portion including a concave portion extending circumferentially around an outer surface of the strain relief portion at a position that overlaps a distal-most end of the hub in an axial direction to permit the concave portion to be used as a reference for measuring a kink generation angle; and
   a dilator that is provided with a dilator main body which is insertable into a lumen of the tube body,
   wherein a material, of which the dilator main body is made, has flexural modulus higher than that of a material of which the tube body is made.

9. The introducer according to claim 8,
   wherein the tube body is provided with a tapered tube distal portion and a tube main body portion positioned on the proximal side of the tube distal portion, and
   wherein a ratio of a thickness to an inner diameter of the tube main body portion is 1/16 or lower, and a ratio of a kink radius to an outer diameter of the tube main body portion is 9.5 or lower.

10. The introducer according to claim 9,
    wherein the tapered tube distal portion of the tube body is harder than the tube main body portion.

11. The introducer according to claim 10,
    wherein the tube body is configured to have a proximal end of the tube body that is fixed to a lumen of the hub, and the kink generation angle is 38° or larger when the tube body is pressed at a position that is 3 cm away from the distal end of the hub in a state in which the strain relief portion is provided.

12. The introducer according to claim 9,
wherein the tube body is configured to have a proximal end of the tube body that is fixed to a lumen of the hub, and the kink generation angle is 38° or larger when the tube body is pressed at a position that is 3 cm away from the distal end of the hub in a state in which the stress relief portion is provided.

13. The introducer according to claim 8, wherein the tube body is configured to have a proximal end of the tube body that is fixed to a lumen of the hub, and the kink generation angle is 38° or larger then the tube body is pressed at a position that is 3 cm away from the distal end of the hub in a state in which the strain relief portion is provided.

14. The introducer according to claim 8, wherein the strain relief portion is supported on a distal side of the hub and surrounds a proximal portion of the tube body.

15. An introducer sheath comprising:
a tube body configured to be percutaneously inserted into a body lumen, wherein the tube body comprises a polyvinylidene fluoride resin;
a hub that is connected to a proximal portion of the tube body;
a strain relief portion that is externally fitted to the tube body and hub, the strain relief portion covering an interlock portion in which the tube body is interlocked with the hub, wherein the strain relief portion including a concave portion extending circumferentially around an outer surface of the strain relief portion at a position that overlaps a distal-most end of the hub in an axial direction to permit the concave portion to be used as a reference for measuring a kink generation angle; and
wherein the tube body has a ratio of a thickness of the tube body to an inner diameter of the tube body of 1/16 or lower over an entire length in an axial direction of the tube body, a ratio of a kink radius to an outer diameter of the tube body of 9.5 or lower, and the tube body does not have a tapered distal portion.

16. The introducer sheath according to claim 15, further comprising:
wherein the tube body is configured to have a proximal end of the tube body that is fixed to a lumen of the hub, and the kink generation angle is 38° or larger when the tube body is pressed at a position that is 3 cm away from the distal end of the hub in a state in which the strain relief portion is provided.

17. The introducer sheath according to claim 15, wherein the strain relief portion is supported on a distal side of the hub and surrounds a proximal portion of the tube body.

\* \* \* \* \*